United States Patent [19]

Hechenbleikner et al.

[11] 4,290,976

[45] Sep. 22, 1981

[54] PROCESS FOR THE PREPARATION OF PHENOL-FREE PHOSPHITES

[75] Inventors: Ingenuin Hechenbleikner, West Cornwall, Conn.; James D. Klicker, Morgantown, W. Va.; William P. Enlow, Falls Village, Conn.

[73] Assignee: Borg-Warner Chemicals, Inc., Parkersburg, W. Va.

[21] Appl. No.: 707,576

[22] Filed: Jul. 22, 1976

Related U.S. Application Data

[63] Continuation-in-part of Ser. No. 561,129, Mar. 24, 1975, abandoned.

[51] Int. Cl.³ .............................................. C07F 9/15
[52] U.S. Cl. ................................ 260/973; 260/927 R
[58] Field of Search ............................ 260/927 R, 973

[56] References Cited

U.S. PATENT DOCUMENTS

| | | | |
|---|---|---|---|
| 2,961,454 | 11/1960 | Gould | 260/927 R |
| 3,192,243 | 6/1965 | Gagliani | 260/927 R |
| 3,201,437 | 8/1965 | Friedman | 260/927 R |
| 3,210,398 | 10/1965 | Rätz | 260/927 R |
| 3,968,188 | 7/1976 | Birum et al. | 260/976 |

OTHER PUBLICATIONS

Mukmenev et al., Doklady. Akad. Nauk. SSSR, vol. 153, No. 3 (11–1963), pp. 605–607.
Gubaidullin et al., dzv. Akad. SSSR, Ser. Khim. (1973) pp. 1116–1118.
Lucas et al., JACS, vol. 72 (1950), pp. 5491–5497.
Derwent Belgium Patents Report, No. 31/65, 5:2–5:3 (8-27-65).

*Primary Examiner*—Richard Raymond
*Attorney, Agent, or Firm*—Joseph Shekleton

[57] ABSTRACT

A process for the preparation of dialkylpentaerythritol diphosphites which are not contaminated by the presence of phenol. The process utilizes dichloropentaerythritol diphosphite as a starting material and since it does not contain a phenyl group there is no possibility of phenol being formed as a contaminant. Furthermore, the product obtained in this fashion is characterized by an enhanced hydrolytic stability.

4 Claims, No Drawings

PROCESS FOR THE PREPARATION OF PHENOL-FREE PHOSPHITES

This application is a continuation-in-part of application Ser. No. 561,129, filed Mar. 24, 1975, and now abandoned. This invention relates to novel organic phosphite compositions. More particularly, it relates to such compositions which are useful as stabilizers of vinyl polymers, especially vinyl chloride polymers and polyolefins.

The purpose of stabilizers is to prevent deterioration of the polymers during processing at high temperatures, and also to permit manufacture of products with increased intrinsic quality because of the enhancement of their resistance to thermal and light degradation during use. In addition, because of the ability of these products to withstand more rigorous conditions, their versatility is increased and new areas of application are thereby opened.

Dialkyl pentaerythritol diphosphites having the structural formula

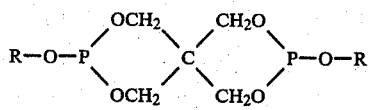

where R and R are alkyl groups have been known for some time as effective stabilizers for vinyl polymers. They have been used primarily to stabilize vinyl chloride polymers and polyolefins, but have found use also in the stabilization of styrene polymers such as ABS.

Despite such wide usage, however, this type of stabilizer, i.e., the dialkyl pentaerythritol diphosphites, has not been entirely satisfactory. The reason for this is the fact that, because of its method of preparation, it inevitably is contaminated with phenol or phenol precut sets. Even a trace of phenol is objectionable in some applications, because of its easily detectable odor.

Also, these dialkyl pentaerythritol diphosphites have not themselves been characterized by good hydrolytic stability. That is, in a moist environment they tend to undergo hydrolytic decomposition, with a corresponding loss of polymer-stabilizing effectiveness. Attempts to solve this problem of hydrolysis have utilized additives and these have been somewhat successful, but the problem remains.

The method of preparing dialkyl pentaerythritol diphosphites heretofore has involved, first, the reaction of triphenyl phosphite with pentaerythritol to give diphenyl pentaerythritol diphosphite, then, reaction of this intermediate with an alcohol such as stearyl alcohol to give the desired product, as follows:

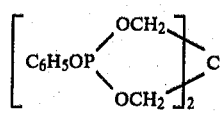

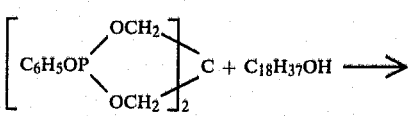

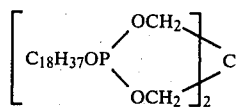

Unfortunately, the product of such as transesterification contains some residual trace amounts of phenol or phenoxy groups which cannot be easily removed. One important objection to such contamination is based upon the use of vinyl chloride polymers in food applications, e.g., in the manufacture of food containers such as bottles.

It is accordingly a principal object of the present invention to provide a phenol-free phosphite stabilizer for polymer compositions.

It is another object of the present invention to provide a phenol-free dialkyl pentaerythritol diphosphite.

These and other objects are accomplished by a process for preparing phenol or phenoxy free dialkyl pentaerythritol diphosphite comprising reacting an alcohol having 10–20 carbon atoms with dichloropentaerythritol diphosphite. The reaction is illustrated as follows:

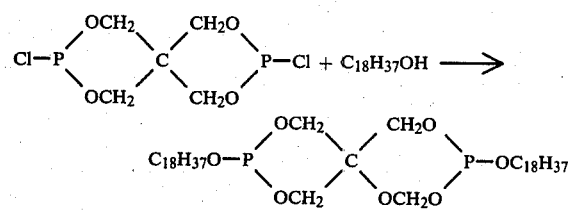

The process proceeds smoothly at moderate temperatures and gives good yields of the desired product. An HCl acceptor is employed in the reaction mixture.

The availability of dichloropentaerythritol diphosphite was first described in some detail by Lucas et al in 72 J. Am. Chem. Soc., 5491 (1950). It is prepared by the reaction of pentaerythritol with phosphorus trichloride, usually in a solvent such as benzene or methylene chloride. See U.S. Pat. No. 3,192,243 (Gagliani) and U.S. Pat. No. 3,210,398 (Ratz). The product may be purified by distillation or crystallization. The pure, colorless crystalline material melts at 121°–123° C.

The reaction of dichloropentaerythritol diphosphite with ethanol in chloroform solution is shown in the Lucas et al. article. A yield of 70% is reported and 4-ethylmorpholine is used as an HCl acceptor.

In the process of this invention, reaction of the dichloropentaerythritol diphosphite with the alcohol is generally carried out with a slight excess of the alcohol. The excess alcohol is permitted to remain in the final product, especially in the case of the higher molecular weight alcohols, giving it a desirably friable character.

The HCl acceptor is an amine or an aqueous alkaline material. Illustrative amines include trimethyl amine, triethyl amine, tri-n-butyl amine, methyl diethyl amine, dimethyl aniline, dimethyl n-octadecyl amine, and dimethyl dodecyl amine. Tertiary amines are preferred, especially tertiary aliphatic amines, and particularly those tertiary aliphatic amines having less than ten carbon atoms. Suitable aqueous alkaline HCl acceptors include sodium carbonate, sodium hydroxide, potassium carbonate and the like. Approximately equal molar amounts of the HCl acceptor should be used, with respect to the amount of alcohol. It will be noted that this is about, or slightly more than the amount of dichloropentaerythritol diphosphite, on a molar basis.

Generally a solvent is used, because it facilitates the isolation of the desired product, i.e., it permits efficient filtration of the product mixture to remove the amine hydrochloride. Preferred solvents include benzene, toluene, xylene, methyl ethyl ketone, acetone and the like. Low-boiling solvents are preferred so as to assist in recycling operations. For the same reason, low-boiling amine HCl acceptors are also preferred.

The alcohol reactant is as indicated one having 10-20 carbon atoms. Illustrative examples include decyl, dodecyl, tetradecyl, hexadecyl, octadecyl and eicosyl alcohols. Decyl and octadecyl alcohols are preferred because the di-decyl and di-octadecyl products are especially valuable polymer stabilizers.

The temperature of the process may range from about 20° C. to about 200° C. although temperatures above about 75° C. tend to favor conversion of the desired product (the spiro form) to an isomer (the caged form) according to the following equilibrium equation:

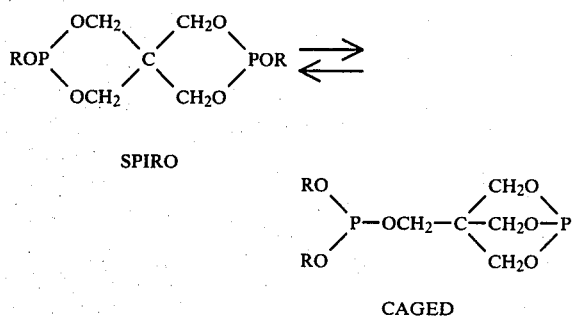

SPIRO

CAGED where R is alkyl.

The process is operable at temperatures as low as about 20° C.

The amine can be recycled in the process merely by regenerating it from the hydrochloride and drying it. Also, the solvent is easily recoverable for reuse.

Another advantage of the present process is the fact that it makes available a product having an increased proportion of the spiro isomer. A typical distearyl pentaerythritol diphosphite, prepared from diphenyl pentaerythritol diphosphite, for example, will contain about equal proportions of the spiro isomer and the caged isomer. The process of this invention, on the other hand, yields a distearyl pentaerythritol diphosphite having only a negligible proportion of caged isomer. As noted above, the spiro isomer is preferred, because of its superior hydrolytic stability.

Also, the products of the process herein are characterized by higher set points and melting points. This is an important advantage because most of these products are relatively low-melting solids and are thus somewhat difficult to handle in large quantities. An increase of 10°-20° C. in a set point of such a material renders it much more friable and easier to handle.

Still further, the purity of the product of the process is greater than similar products of the prior art. The prior art products contained significant quantities of trialkyl phosphite and these are much reduced in the products of the present process.

The process of the invention is illustrated by the following example which is not, however, to be construed as limiting in any way.

EXAMPLE 1

To a stirred solution of 567 g. (2.1 mols) of octadecyl alcohol and 212 g. (2.1 mols) of triethyl amine in 1800 ml. of toluene, at 30° C., there is added a solution of 265 g. (1.0 mol) of dichloropentaerythritol diphosphite in 600 ml. of toluene; the addition is made portionwise over a period of one hour, then the mixture is warmed with continued stirring at 45°-50° C. The cooled mixture is filtered to separate the triethylamine hydrochloride and the filtrate is stripped of toluene to a final temperature of 85° C./20 mm. The solid residue consitutes a quantitative yield of distearyl pentaerythritol diphosphite, M.P., 68°-70° C.

Alternatively, the triethylamine hydrochloride can be separated by adding water to the cooled mixture above, while stirring, and drawing off the toluene fraction.

We claim:

1. A process for preparing phenol-free dialkyl pentaerythritol diphosphite comprising reacting an alcohol having 10-20 carbon atoms with a pentaerythritol diphosphite having the structure

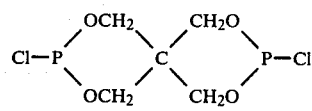

2. The process of claim 1 wherein the alcohol and dichloropentaerythritol diphosphite are reacted in the presence of an HCl acceptor.

3. The process of claim 1 wherein the alcohol is decyl alcohol.

4. The process of claim 1 wherein the alcohol is octadecyl alcohol.

* * * * *